(12) United States Patent
Cao et al.

(10) Patent No.: US 11,904,187 B2
(45) Date of Patent: Feb. 20, 2024

(54) IMAGING METHODS USING MULTIPLE RADIATION BEAMS

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 112 days.

(21) Appl. No.: 17/368,445

(22) Filed: Jul. 6, 2021

(65) Prior Publication Data

US 2023/0010663 A1    Jan. 12, 2023

(51) Int. Cl.
*A61B 6/00* (2006.01)
*A61N 5/10* (2006.01)

(52) U.S. Cl.
CPC ......... *A61N 5/1082* (2013.01); *A61N 5/1079* (2013.01); *A61N 5/1084* (2013.01)

(58) Field of Classification Search
CPC ...... A61N 5/10; A61N 5/1082; A61N 5/1079; A61N 5/1084; A61B 6/5205; A61B 6/4085; A61B 6/4007; A61B 6/4233; G01T 1/20182; G01T 1/243; G01T 1/29
See application file for complete search history.

(56) References Cited

U.S. PATENT DOCUMENTS 8,797,432 B2 * 8/2014 Cho ................... H01L 27/14634
348/294
8,867,702 B2 * 10/2014 Nishino ............... A61B 6/4283
378/92

* cited by examiner

*Primary Examiner* — Jurie Yun
(74) *Attorney, Agent, or Firm* — IPRO, PLLC; Qian Gu

(57) ABSTRACT

Disclosed herein is a method comprising: generating multiple radiation beams respectively from multiple locations toward an object and an image sensor, wherein the image sensor comprises an array of multiple active areas, and gaps among the multiple active areas, and capturing multiple partial images of the object with the image sensor using respectively radiations of the multiple radiation beams that have passed through and interacted with the object, wherein each point of the object is captured in at least one partial image of the multiple partial images.

22 Claims, 9 Drawing Sheets

810: generating 3 radiation beams respectively from 3 locations toward an object and an image sensor, wherein the image sensor comprises (A) an array of M×N active areas, and (B) gaps among the M×N active areas and running in a first direction and a second direction, and wherein the first direction is perpendicular to the second direction.

820: capturing 3 partial images of the object with the image sensor using respectively radiations of the 3 radiation beams that have passed through and interacted with the object, wherein each point of the object is captured in at least one partial image of the 3 partial images, and wherein M and N are integers greater than 1.

910: generating 2 radiation beams respectively from 2 locations toward an object and an image sensor, wherein the image sensor comprises (A) an array of 1×N active areas, and (B) gaps among the 1×N active areas and running in a direction.

920: capturing 2 partial images of the object with the image sensor using respectively radiations of the 2 radiation beams that have passed through and interacted with the object, wherein each point of the object is captured in at least one partial image of the 2 partial images, and wherein N is an integer greater than 1.

FIG. 9

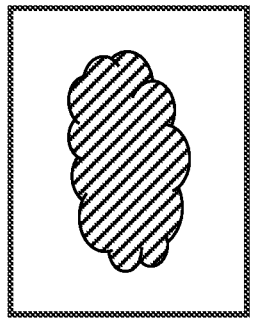
Stitched image of the object
Fig. 10C
  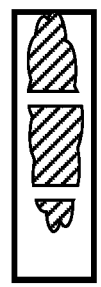
Partial images of an object captured using radiation beam from 2 locations
Fig. 10B
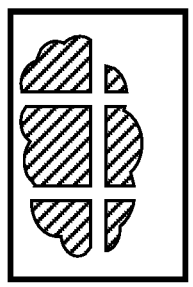 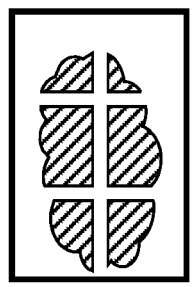 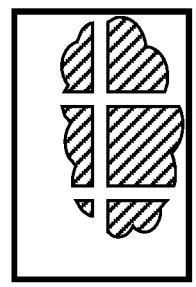
Partial images of an object captured using radiation beam from 3 locations
Fig. 10A

IMAGING METHODS USING MULTIPLE RADIATION BEAMS

BACKGROUND

A radiation detector is a device that measures a property of a radiation. Examples of the property may include a spatial distribution of the intensity, phase, and polarization of the radiation. The radiation may be one that has interacted with an object. For example, the radiation measured by the radiation detector may be a radiation that has penetrated the object. The radiation may be an electromagnetic radiation such as infrared light, visible light, ultraviolet light, X-ray, or γ-ray. The radiation may be of other types such as α-rays and β-rays. An imaging system may include one or more image sensors each of which may have multiple radiation detectors.

SUMMARY

Disclosed herein is a method, comprising: generating 3 radiation beams respectively from 3 locations toward an object and an image sensor, wherein the image sensor comprises (A) an array of M×N active areas, and (B) gaps among the M×N active areas and running in a first direction and a second direction, and wherein the first direction is perpendicular to the second direction; and capturing 3 partial images of the object with the image sensor using respectively radiations of the 3 radiation beams that have passed through and interacted with the object, wherein each point of the object is captured in at least one partial image of the 3 partial images, and wherein M and N are integers greater than 1.

In an aspect, the method further comprises, after said capturing the 3 partial images of the object is performed, stitching the 3 partial images resulting in a stitched image of the object.

In an aspect, said stitching the 3 partial images comprises projecting at least one partial image of the 3 partial images from one plane to another plane.

In an aspect, the 3 locations are on a common plane parallel to a surface plane that intersects all sensing elements of the M×N active areas.

In an aspect, a ratio of a distance between any two locations of the 3 locations to a distance between the common plane and the surface plane is less than 0.1, less than 0.05, less than 0.02, or less than 0.01.

In an aspect, a straight line connecting any two locations of the 3 locations is not parallel to the first direction and is not parallel to the second direction.

In an aspect, all the 3 locations are on a straight line.

In an aspect, a first ratio of a distance between the first and second locations to a maximum gap width of the gaps is less than 1.5, less than 1.6, less than 1.7, or less than 2, and a second ratio of a distance between the second and third locations to the maximum gap width of the gaps is less than 1.5, less than 1.6, less than 1.7, or less than 2.

In an aspect, both the first ratio and the second ratio are in a range of 1.4 to 1.5.

In an aspect, the 3 radiation beams are generated one by one.

In an aspect, the 3 radiation beams are X-ray beams.

In an aspect, the 3 radiation beams are cone beams.

Disclosed herein is a method, comprising: generating 2 radiation beams respectively from 2 locations toward an object and an image sensor, wherein the image sensor comprises (A) an array of 1×N active areas, and (B) gaps among the 1×N active areas and running in a direction; and capturing 2 partial images of the object with the image sensor using respectively radiations of the 2 radiation beams that have passed through and interacted with the object, wherein each point of the object is captured in at least one partial image of the 2 partial images, and wherein N is an integer greater than 1.

In an aspect, the method further comprises, after said capturing the 2 partial images of the object is performed, stitching the 2 partial images resulting in a stitched image of the object.

In an aspect, said stitching the 2 partial images comprises projecting at least one partial image of the 2 partial images from one plane to another plane.

In an aspect, the 2 locations are on a common plane parallel to a surface plane that intersects all sensing elements of the 1×N active areas.

In an aspect, a ratio of a distance between the 2 locations to a distance between the common plane and the surface plane is less than 0.1, less than 0.05, less than 0.02, or less than 0.01.

In an aspect, a straight line connecting the 2 locations is not parallel to the direction.

In an aspect, the straight line connecting the 2 locations is perpendicular to the direction.

In an aspect, a ratio of a distance between the 2 locations to a maximum gap width of the gaps is less than 1.1, less than 1.2, less than 1.5, or less than 2.

In an aspect, the ratio is 1.

In an aspect, the 2 radiation beams are generated one by one.

In an aspect, the 2 radiation beams are X-ray beams.

In an aspect, the 2 radiation beams are cone beams.

BRIEF DESCRIPTION OF FIGURES

FIG. 8 shows a flowchart generalizing the operation of the image sensor.

FIG. 9 shows a flowchart generalizing the operation of the image sensor according to an alternative scenario.

FIGS. 10A-10C schematically shows 3 partial images, 2 partial images and a stitched image of an object.

DETAILED DESCRIPTION

Radiation Detector

Figure 1:
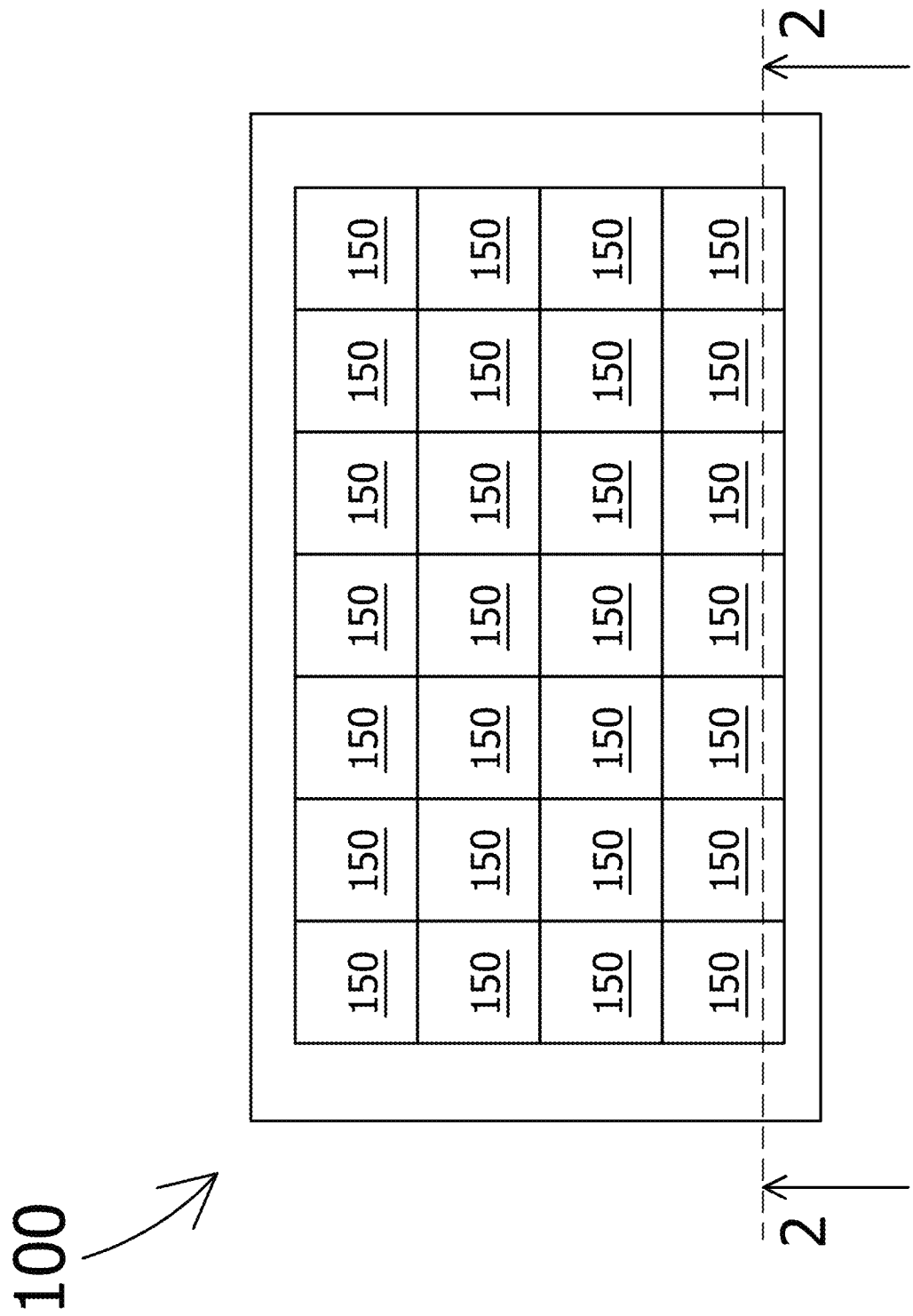
FIG. 1 schematically shows a radiation detector, according to an embodiment.

FIG. 1 schematically shows a radiation detector 100, as an example. The radiation detector 100 may include an array of pixels 150 (also referred to as sensing elements 150). The array may be a rectangular array (as shown in FIG. 1), a honeycomb array, a hexagonal array, or any other suitable array. The array of pixels 150 in the example of FIG. 1 has 4 rows and 7 columns; however, in general, the array of pixels 150 may have any number of rows and any number of columns.

Each pixel 150 may be configured to detect radiation from a radiation source (not shown) incident thereon and may be configured to measure a characteristic (e.g., the energy of the particles, the wavelength, and the frequency) of the radiation. A radiation may include particles such as photons and subatomic particles. Each pixel 150 may be configured to count numbers of particles of radiation incident thereon whose energy falls in a plurality of bins of energy, within a period of time. All the pixels 150 may be configured to count the numbers of particles of radiation incident thereon within a plurality of bins of energy within the same period of time. When the incident particles of radiation have similar energy, the pixels 150 may be simply configured to count numbers of particles of radiation incident thereon within a period of time, without measuring the energy of the individual particles of radiation.

Each pixel 150 may have its own analog-to-digital converter (ADC) configured to digitize an analog signal representing the energy of an incident particle of radiation into a digital signal, or to digitize an analog signal representing the total energy of a plurality of incident particles of radiation into a digital signal. The pixels 150 may be configured to operate in parallel. For example, when one pixel 150 measures an incident particle of radiation, another pixel 150 may be waiting for a particle of radiation to arrive. The pixels 150 may not have to be individually addressable.

The radiation detector 100 described here may have applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this radiation detector 100 in place of a photographic plate, a photographic film, a PSP plate, an X-ray image intensifier, a scintillator, or another semiconductor X-ray detector.

Figure 2:
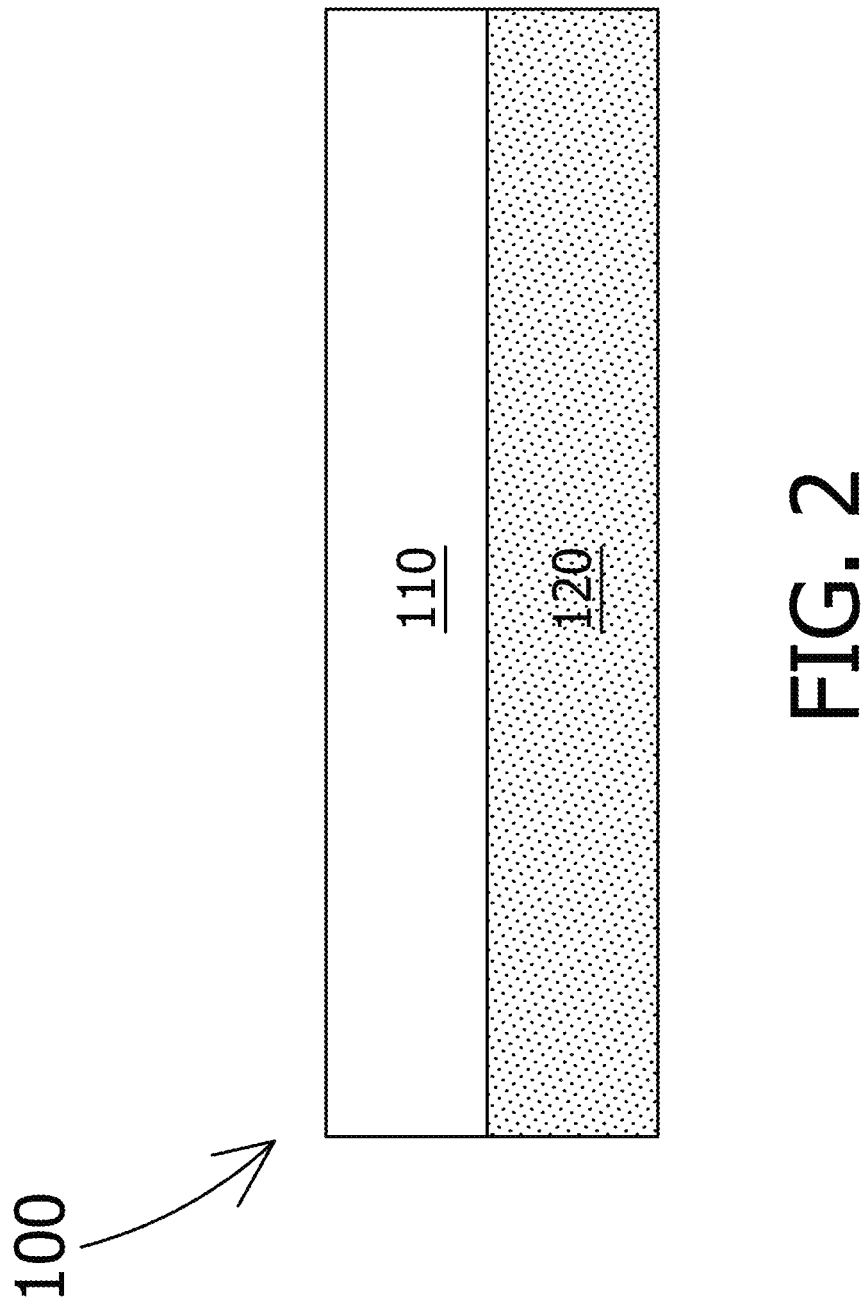
FIG. 2 schematically shows a simplified cross-sectional view of the radiation detector, according to an embodiment.

FIG. 2 schematically shows a simplified cross-sectional view of the radiation detector 100 of FIG. 1 along a line 2-2, according to an embodiment. Specifically, the radiation detector 100 may include a radiation absorption layer 110 and an electronics layer 120 (which may include one or more ASICs or application-specific integrated circuits) for processing or analyzing electrical signals which incident radiation generates in the radiation absorption layer 110. The radiation detector 100 may or may not include a scintillator (not shown). The radiation absorption layer 110 may include a semiconductor material such as silicon, germanium, GaAs, CdTe, CdZnTe, or a combination thereof. The semiconductor material may have a high mass attenuation coefficient for the radiation of interest.

Figure 3:
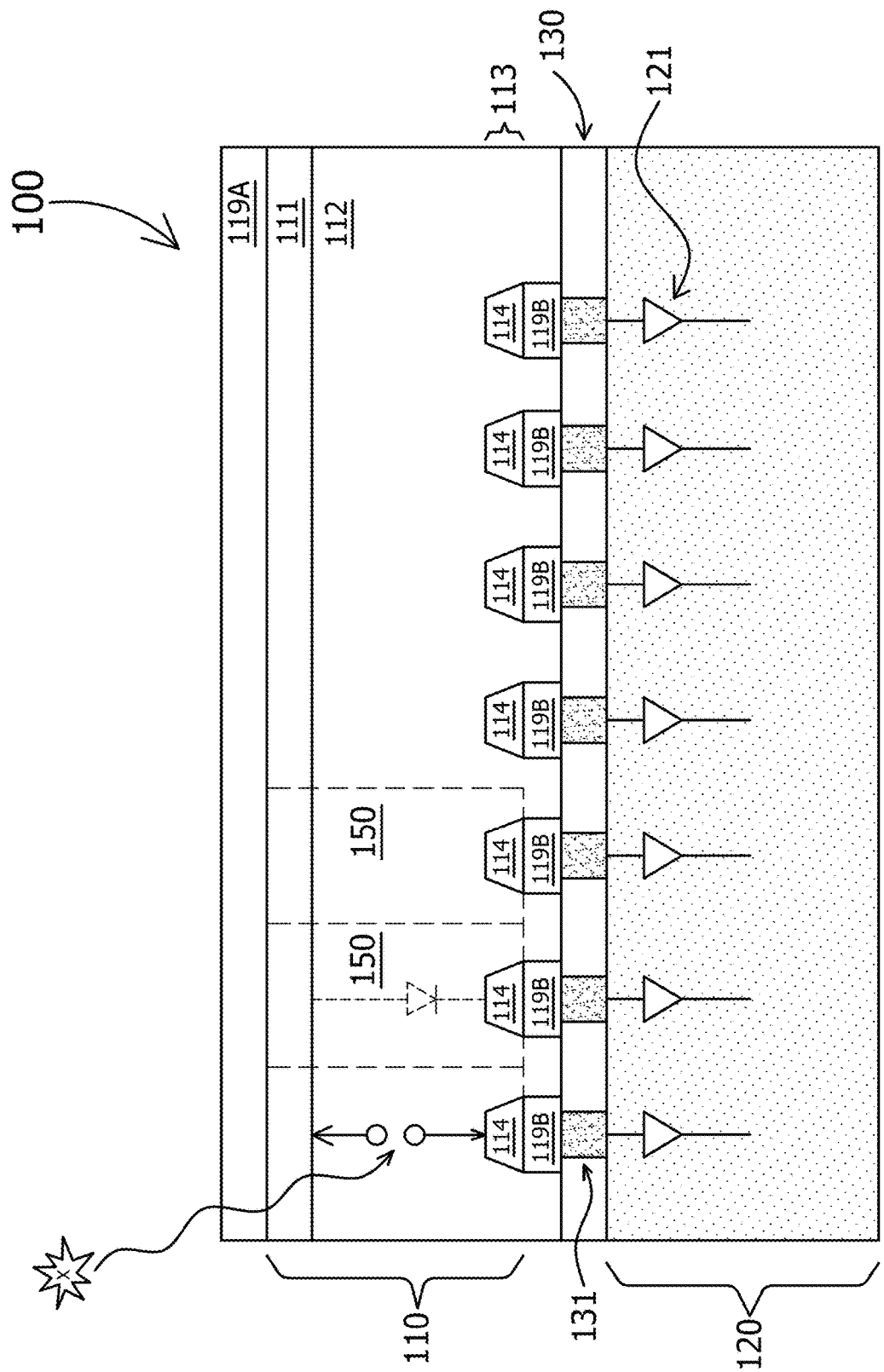
FIG. 3 schematically shows a detailed cross-sectional view of the radiation detector, according to an embodiment.

FIG. 3 schematically shows a detailed cross-sectional view of the radiation detector 100 of FIG. 1 along the line 2-2, as an example. Specifically, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional intrinsic region 112. The discrete regions 114 may be separated from one another by the first doped region 111 or the intrinsic region 112. The first doped region 111 and the second doped region 113 may have opposite types of doping (e.g., region 111 is p-type and region 113 is n-type, or region 111 is n-type and region 113 is p-type). In the example of FIG. 3, each of the discrete regions 114 of the second doped region 113 forms a diode with the first doped region 111 and the optional intrinsic region 112. Namely, in the example in FIG. 3, the radiation absorption layer 110 has a plurality of diodes (more specifically, 7 diodes corresponding to 7 pixels 150 of one row in the array of FIG. 1, of which only 2 pixels 150 are labeled in FIG. 3 for simplicity). The plurality of diodes may have an electrical contact 119A as a shared (common) electrode. The first doped region 111 may also have discrete portions.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessor, and memory. The electronic system 121 may include one or more ADCs (analog to digital converters). The electronic system 121 may include components shared by the pixels 150 or components dedicated to a single pixel 150. For example, the electronic system 121 may include an amplifier dedicated to each pixel 150 and a microprocessor shared among all the pixels 150. The electronic system 121 may be electrically connected to the pixels 150 by vias 131. Space among the vias may be filled with a filler material 130, which may increase the mechanical stability of the connection of the electronics layer 120 to the radiation absorption layer 110. Other bonding techniques are possible to connect the electronic system 121 to the pixels 150 without using the vias 131.

When radiation from the radiation source (not shown) hits the radiation absorption layer 110 including diodes, particles of the radiation may be absorbed and generate one or more charge carriers (e.g., electrons, holes) by a number of mechanisms. The charge carriers may drift to the electrodes of one of the diodes under an electric field. The electric field may be an external electric field. The electrical contact 119B may include discrete portions each of which is in electrical contact with the discrete regions 114. The term "electrical contact" may be used interchangeably with the word "electrode." In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel 150.

Figure 4:
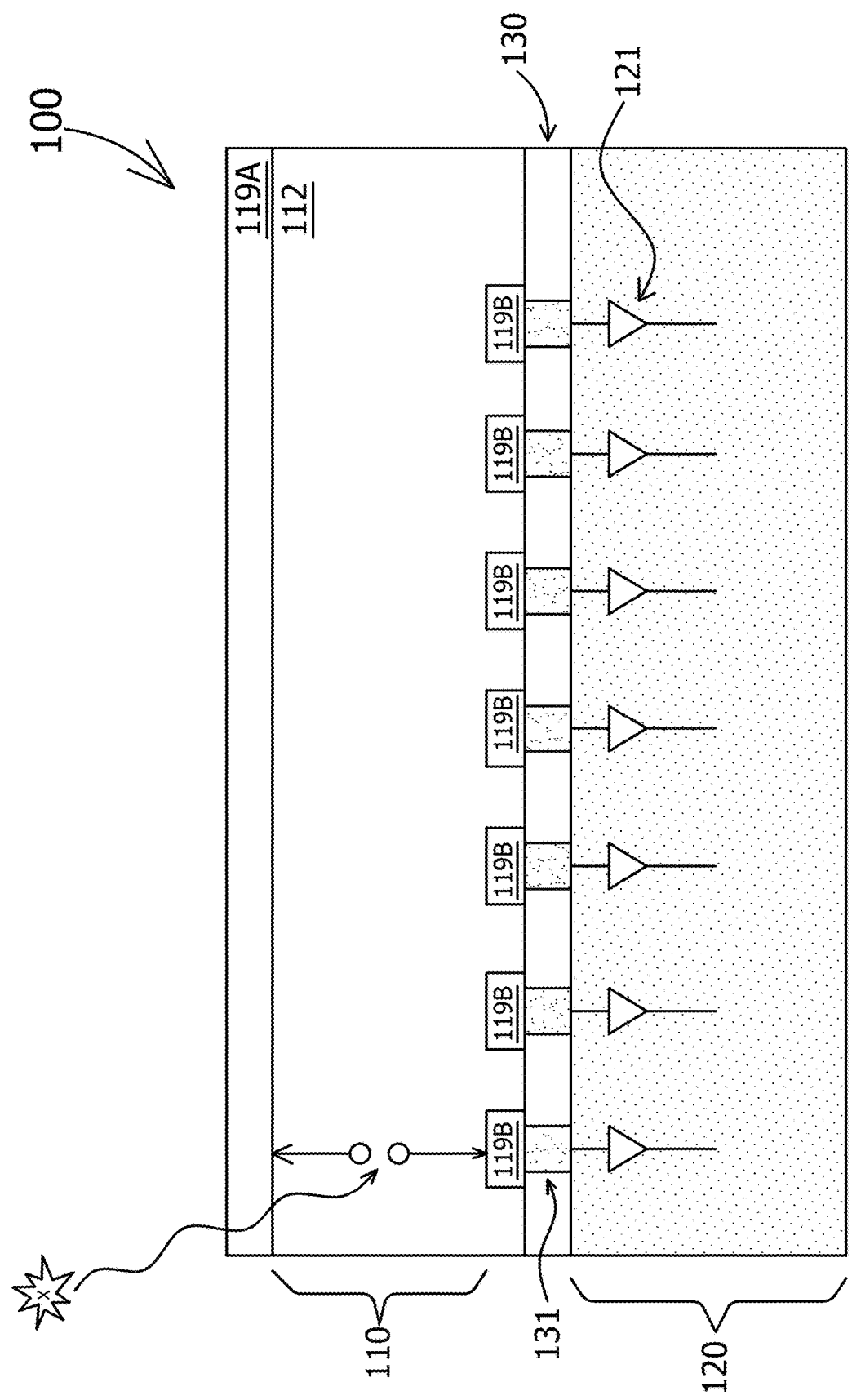
FIG. 4 schematically shows a detailed cross-sectional view of the radiation detector, according to an alternative embodiment.

FIG. 4 schematically shows a detailed cross-sectional view of the radiation detector 100 of FIG. 1 along the line 2-2, according to an alternative embodiment. More specifically, the radiation absorption layer 110 may include a resistor of a semiconductor material such as silicon, germanium, GaAs, CdTe, CdZnTe, or a combination thereof, but does not include a diode. The semiconductor material may have a high mass attenuation coefficient for the radiation of interest. In an embodiment, the electronics layer 120 of FIG. 4 is similar to the electronics layer 120 of FIG. 3 in terms of structure and function.

When the radiation hits the radiation absorption layer 110 including the resistor but not diodes, it may be absorbed and generate one or more charge carriers by a number of mechanisms. A particle of the radiation may generate 10 to 100,000 charge carriers. The charge carriers may drift to the electrical contacts 119A and 119B under an electric field. The electric field may be an external electric field. The electrical contact 119B may include discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

Radiation Detector Package

Figure 5:
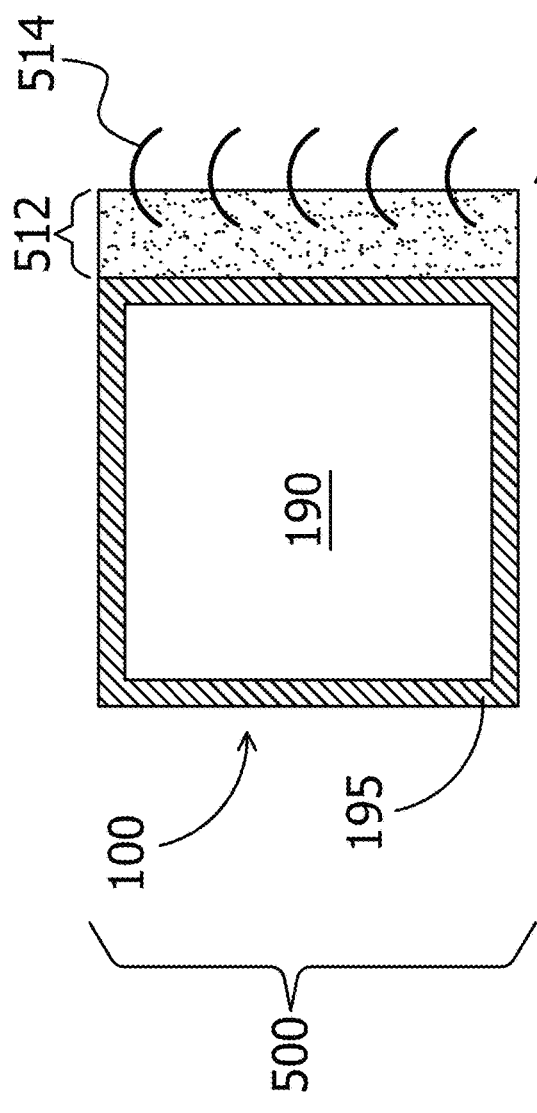
FIG. 5 schematically shows a top view of a package including the radiation detector and a printed circuit board (PCB), according to an embodiment.

FIG. 5 schematically shows a top view of a package 500 including the radiation detector 100 and a printed circuit board (PCB) 510. The term "PCB" as used herein is not limited to a particular material. For example, a PCB may include a semiconductor. The radiation detector 100 may be mounted to the PCB 510. The wiring between the radiation detector 100 and the PCB 510 is not shown for the sake of clarity. The PCB 510 may have one or more radiation detectors 100. The PCB 510 may have an area 512 not covered by the radiation detector 100 (e.g., for accommodating bonding wires 514). The radiation detector 100 may have an active area 190 which is where the pixels 150 (FIG. 1) are located. The radiation detector 100 may have a perimeter zone 195 near the edges of the radiation detector 100. The perimeter zone 195 has no pixels 150, and the radiation detector 100 does not detect particles of radiation incident on the perimeter zone 195.

Image Sensor

Figure 6:
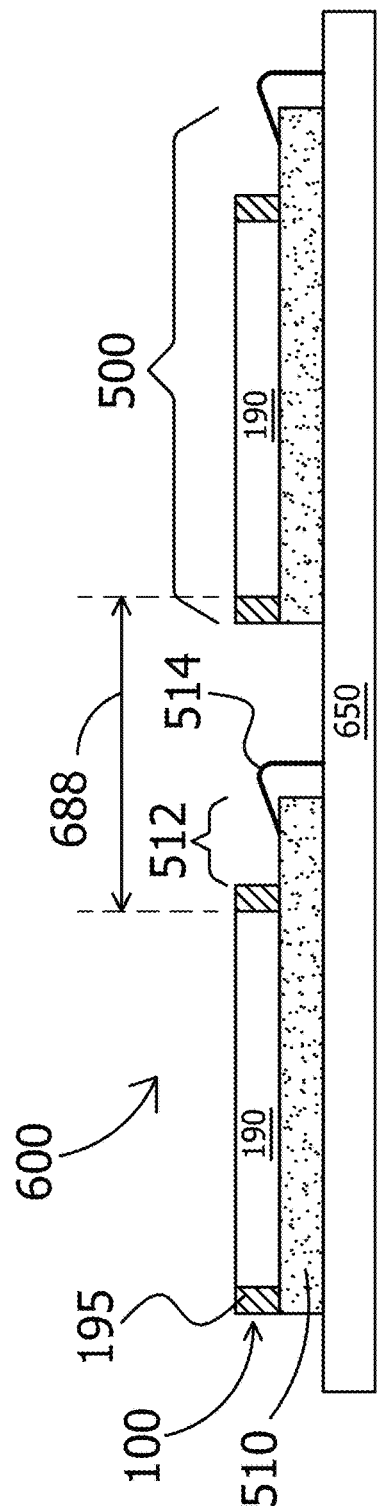
FIG. 6 schematically shows a cross-sectional view of an image sensor including the packages of FIG. 5 mounted to a system PCB (printed circuit board), according to an embodiment.

FIG. 6 schematically shows a cross-sectional view of an image sensor 600, according to an embodiment. The image sensor 600 may include one or more packages 500 of FIG. 5 mounted to a system PCB 650. FIG. 6 shows 2 packages 500 as an example. The electrical connection between the PCBs 510 and the system PCB 650 may be made by bonding wires 514. In order to accommodate the bonding wires 514 on the PCB 510, the PCB 510 may have the area 512 not covered by the radiation detector 100. In order to accommodate the bonding wires 514 on the system PCB 650, the packages 500 may have gaps in between. The gaps may be approximately 1 mm or more. Particles of radiation incident on the perimeter zones 195, on the area 512, or on the gaps cannot be detected by the packages 500 on the system PCB 650. A dead zone of a radiation detector (e.g., the radiation detector 100) is the area of the radiation-receiving surface of the radiation detector, on which incident particles of radiation cannot be detected by the radiation detector. A dead zone of a package (e.g., package 500) is the area of the radiation-receiving surface of the package, on which incident particles of radiation cannot be detected by the radiation detector or detectors in the package. In this example shown in FIG. 5 and FIG. 6, the dead zone of the package 500 includes the perimeter zones 195 and the area 512. A dead zone (e.g., 688) of an image sensor (e.g., image sensor 600) with a group of packages (e.g., packages 500 mounted on the same PCB and arranged in the same layer or in different layers) includes the combination of the dead zones of the packages in the group and the gaps between the packages.

In an embodiment, the radiation detector 100 (FIG. 1) operating by itself may be considered an image sensor. In an embodiment, the package 500 (FIG. 5) operating by itself may be considered an image sensor.

The image sensor 600 including the radiation detectors 100 may have the dead zone 688 incapable of detecting incident radiation. However, the image sensor 600 may capture multiple partial images of an object or scene (not shown), and then these captured partial images may be stitched to form an image of the entire object or scene.

Imaging Process—Initial Arrangement

Figure 7:
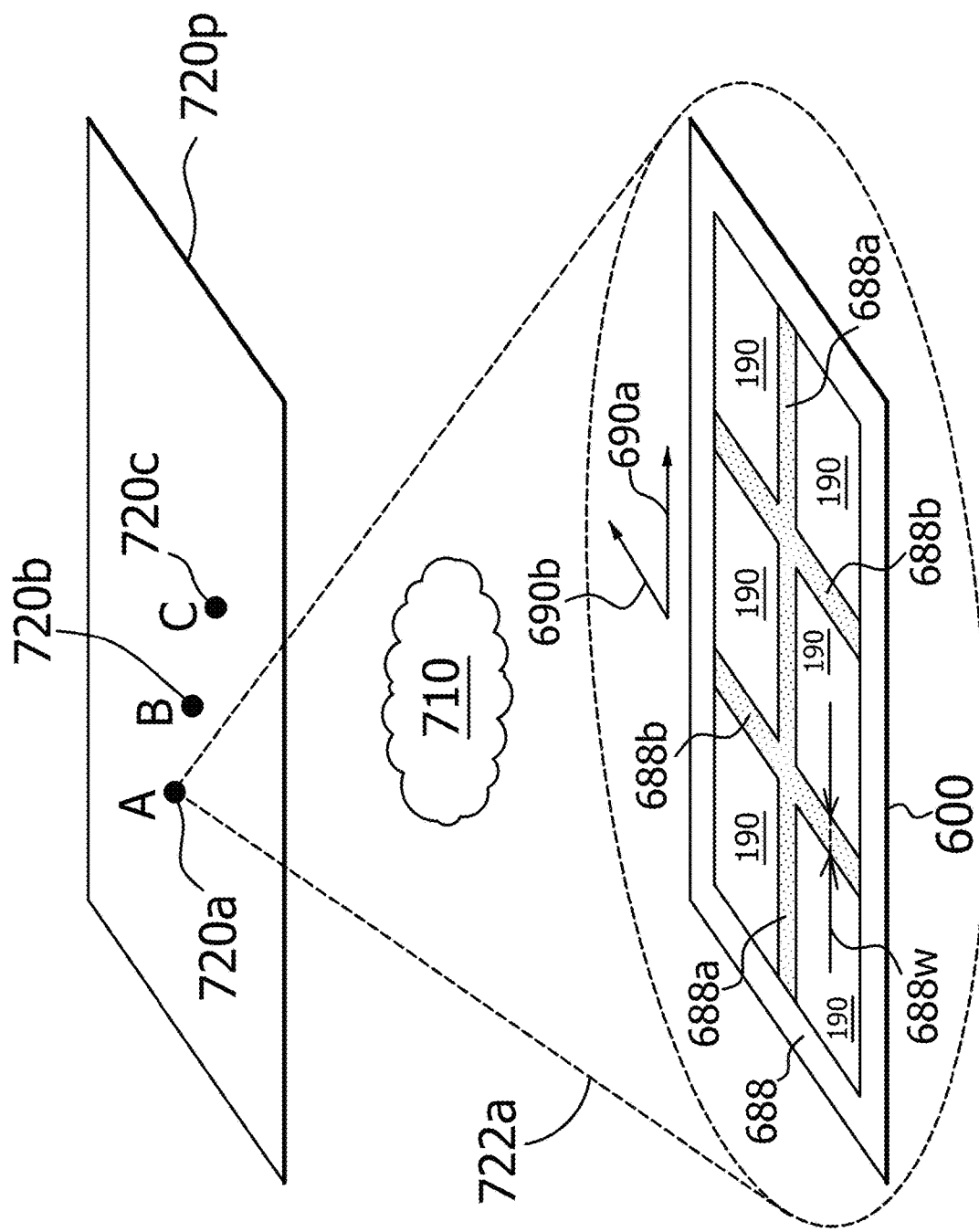
FIG. 7 schematically shows a perspective view of the image sensor in operation, according to an embodiment.

FIG. 7 schematically shows a perspective view of the image sensor 600 of FIG. 6, according to an embodiment. The image sensor 600 may include a rectangular array of 2×3 active areas 190 and the dead zone 688 (other components of the image sensor 600 are not shown for simplicity).

In an embodiment, the dead zone 688 may include multiple gaps with each gap being between 2 adjacent active areas 190. Specifically, the dead zone 688 includes (A) 3 gaps 688a running in a direction 690a and (B) 4 gaps 688b running in a direction 690b. In an embodiment, the direction 690a may be perpendicular to the direction 690b.

In an embodiment, an object 710 may be positioned between the image sensor 600 and radiation sources 720a, 720b, and 720c. The radiation sources 720a, 720b, and 720c may be positioned at locations A, B, and C, respectively.

First Partial Image Capture

In an embodiment, a first partial image capture may be performed as follows. The radiation source 720a may generate a first radiation beam 722a toward the object 710 and the image sensor 600, while the other radiation sources 720b and 720c are disabled (i.e., not generating any radiation). In an embodiment, the first radiation beam 722a may be a cone beam as shown. Other appropriate shapes of the first radiation beam 722a may be used. In an embodiment, the first radiation beam 722a may be an X-ray beam. The first radiation beam 722a may be other appropriate types of radiation.

In an embodiment, using the radiation of the first radiation beam 722a that has passed through and interacted with the object 710, the image sensor 600 may capture a first partial image of the object 710.

Second Partial Image Capture

In an embodiment, after the image sensor 600 captures the first partial image of the object 710, a second partial image capture may be performed as follows. The radiation source 720b may generate a second radiation beam (similar to the first radiation beam 722a, but not shown for simplicity) toward the object 710 and the image sensor 600, while the other radiation sources 720a and 720c are disabled (i.e., not generating any radiation). In an embodiment, the second radiation beam may be a cone beam. In an embodiment, the second radiation beam may be an X-ray beam. The second radiation beam may be offset but not rotated relative to the first radiation beam 722a. The second radiation beam may be offset and rotated relative to the first radiation beam 722a.

In an embodiment, using the radiation of the second radiation beam that has passed through and interacted with the object 710, the image sensor 600 may capture a second partial image of the object 710.

Third Partial Image Capture

In an embodiment, after the image sensor 600 captures the second partial image of the object 710, a third partial image capture may be performed as follows. The radiation source 720c may generate a third radiation beam (similar to the first radiation beam 722a, but not shown for simplicity) toward the object 710 and the image sensor 600, while the other radiation sources 720a and 720b are disabled (i.e., not generating any radiation). In an embodiment, the third radiation beam may be a cone beam. In an embodiment, the third radiation beam may be an X-ray beam.

In an embodiment, using the radiation of the third radiation beam that has passed through and interacted with the object 710, the image sensor 600 may capture a third partial image of the object 710.

In an embodiment, the locations A, B, and C, the object 710, and the image sensor 600 may be arranged such that each point of the object 710 is captured in at least one of the first, second, and third partial images.

Image Stitching

In an embodiment, after the image sensor 600 captures the third partial image of the object 710, the image sensor 600 may stitch the first, second, and third partial images to create a first stitched image of the object 710.

In an embodiment, the stitching of the first, second, and third partial images to create the first stitched image of the object 710 may involve projecting at least one partial image of the first, second, and third partial images from one plane to another plane. For example, the first and second partial images may be projected to the plane of the third partial image. Alternatively, all the first, second, and third partial images may be projected to a common plane.

Flowchart for Generalization

FIG. 8 shows a flowchart 800 generalizing the operation of the image sensor 600 described above. In step 810, three radiation beams are generated respectively from 3 locations toward an object and an image sensor. For example, in the embodiments described above, with reference to FIG. 7, the first, second, and third radiation beams are generated respectively from 3 locations A, B, and C toward the object 710 and the image sensor 600.

In addition, in step 810, the image sensor comprises (A) an array of M×N active areas, and (B) gaps among the M×N active areas and running in a first direction and a second direction. For example, in the embodiments described above, the image sensor 600 includes (A) an array of 2×3 active areas 190, and (B) gaps 688a and 688b among the 2×3 active areas 190 and running in the directions 690a and 690b.

In addition, in step 810, the first direction is perpendicular to the second direction. For example, in the embodiments described above, the direction 690a is perpendicular to the direction 690b.

In step 820, three partial images of the object are captured with the image sensor using respectively radiations of the 3 radiation beams that have passed through and interacted with the object. For example, in the embodiments described above, the first, second, and third partial images of the object 710 are captured with the image sensor 600 using respectively radiations of the first, second, and third radiation beams that have passed through and interacted with the object 710.

In addition, in step 820, each point of the object is captured in at least one partial image of the 3 partial images; and M and N are integers greater than 1. For example, in the embodiments described above, each point of the object 710 is captured in at least one partial image of the first, second, and third partial images; and M=2 and N=3 are integers greater than 1.

Locations A, B, And C are of Same Distance from Image Sensor

In an embodiment, with reference to FIG. 7, the locations A, B, and C may be on a common plane 720p which is parallel to a surface plane (not shown) of the image sensor 600, wherein the surface plane intersects all pixels (sensing elements) 150 (FIG. 1) of the 2×3 active areas 190. In other words, the locations A, B, and C are of the same distance from the image sensor 600.

In an embodiment, the ratio of the distance between any two locations of the 3 locations A, B, and C to the distance between the common plane 720p and the surface plane of the image sensor 600 may be less than 0.1, less than 0.05, less than 0.02, or less than 0.01. The lower this ratio is, the less distortion the first, second, and third partial images incur.

More on the 3 Locations A, B, and C

In an embodiment, with reference to FIG. 7, a straight line connecting any 2 locations of the 3 locations A, B, and C may be not parallel to the direction 690a and not parallel to the direction 690b. In other words, none of the 3 straight line segments AB, BC, and CA is parallel to any one of the directions 690a and 690b.

In an embodiment, the 3 locations A, B, and C may be on a straight line (i.e., colinear).

In an embodiment, a first ratio of the distance between the locations A and B to a maximum gap width 688w of the gaps 688a and 688b may be less than 1.5, less than 1.6, less than 1.7, or less than 2. In an embodiment, a second ratio of the distance between the locations B and C to the maximum gap width 688w of the gaps 688a and 688b may be less than 1.5, less than 1.6, less than 1.7, or less than 2.

In an embodiment, both the first ratio and the second ratio mentioned above may be in the range of 1.4 to 1.5.

Alternative Scenario

In the embodiments described above, with reference to FIG. 7, the image sensor 600 includes an array of 2×3 active areas 190. In an alternative scenario, the image sensor 600 may include an array of 1×3 active areas 190 (i.e., one row of 3 active areas 190). As a result, the dead zone 688 of the image sensor 600 includes 2 gaps 688b running in the direction 690b, and no gaps 688a running in the direction 690a.

In an embodiment of the alternative scenario, two partial image captures may be performed using 2 radiation sources 720a and 720b (i.e., the radiation source 720c is not used) and the image sensor 600 (with the 1×3 active areas 190) as follows.

In an embodiment of the alternative scenario, the radiation source 720a may generate a fourth radiation beam toward the object 710 and the image sensor 600 (with the 1×3 active areas 190), while the radiation source 720b is disabled (i.e., not generating any radiation). Using the radiation of the fourth radiation beam that has passed through and interacted with the object 710, the image sensor 600 (with the 1×3 active areas 190) may capture a fourth partial image of the object 710.

In an embodiment of the alternative scenario, after the image sensor 600 (with the 1×3 active areas 190) captures the fourth partial image of the object 710, the radiation source 720b may generate a fifth radiation beam toward the object 710 and the image sensor 600 (with the 1×3 active areas 190), while the radiation sources 720a is disabled (i.e., not generating any radiation). Using the radiation of the fifth radiation beam that has passed through and interacted with the object 710, the image sensor 600 (with the 1×3 active areas 190) may capture a fifth partial image of the object 710.

In an embodiment of the alternative scenario, the locations A and B, the object 710, and the image sensor 600 (with the 1×3 active areas 190) may be arranged such that each point of the object 710 is captured in at least one of the fourth and fifth partial images.

In an embodiment of the alternative scenario, after the image sensor 600 (with the 1×3 active areas 190) captures the fifth partial image of the object 710, the image sensor 600 (with the 1×3 active areas 190) may stitch the fourth and fifth partial images to create a second stitched image of the object 710.

In an embodiment of the alternative scenario, the stitching of the fourth and fifth partial images to create the second stitched image of the object 710 may involve projecting at least one partial image of the fourth and fifth partial images from one plane to another plane. For example, the fourth partial image may be projected to the plane of the fifth partial image. Alternatively, both the fourth and fifth partial images may be projected to a common plane.

Flowchart for Generalization of Alternative Scenario

FIG. 9 shows a flowchart 900 generalizing the operation of the imaging sensor 600 (with the 1×3 active areas 190) in the alternative scenario described above. In step 910, two radiation beams are generated respectively from 2 locations toward an object and an image sensor. For example, in the alternative scenario described above, the fourth and fifth radiation beams are generated respectively from 2 locations A and B toward the object 710 and the image sensor 600 (with the 1×3 active areas 190).

In addition, in step 910, the image sensor comprises (A) an array of 1×N active areas, and (B) gaps among the 1×N active areas and running in a direction. For example, in the alternative scenario described above, the image sensor 600 (with the 1×3 active areas 190) includes (A) an array of 1×3 active areas 190, and (B) 2 gaps 688b among the 1×3 active areas 190 and running in the direction 690b.

In step 920, two partial images of the object are captured with the image sensor using respectively radiations of the 2 radiation beams that have passed through and interacted with the object. For example, in the alternative scenario described above, the fourth and fifth partial images of the object 710 are captured with the image sensor 600 (with the 1×3 active areas 190) using respectively radiations of the fourth and fifth radiation beams that have passed through and interacted with the object 710.

In addition, in step 920, each point of the object is captured in at least one partial image of the 2 partial images, and N is an integer greater than 1. For example, in the alternative scenario described above, each point of the object 710 is captured in at least one partial image of the fourth and fifth partial images; and N=3 is an integer greater than 1.

Other Embodiments of the Alternative Scenario

In an embodiment of the alternative scenario, with reference to FIG. 7, the locations A and B may be on the common plane 720p which is parallel to a surface plane (not shown) of the image sensor 600 (with the 1×3 active areas 190), wherein the surface plane of the image sensor 600 (with the 1×3 active areas 190) intersects all pixels (sensing elements) 150 (FIG. 1) of the 1×3 active areas 190. In other words, the locations A and B are of the same distance from the image sensor 600 (with the 1×3 active areas 190).

In an embodiment of the alternative scenario, the ratio of the distance between the two locations A and B to the distance between the common plane 720p and the surface plane of the image sensor 600 (with the 1×3 active areas 190) may be less than 0.1, less than 0.05, less than 0.02, or less than 0.01.

In an embodiment of the alternative scenario, with reference to FIG. 7, the straight line segment AB may be not parallel to the direction 690b. In an embodiment of the alternative scenario, the straight line segment AB may be perpendicular to the direction 690b.

In an embodiment of the alternative scenario, a third ratio of the distance between the locations A and B to the maximum gap width 688w of the 2 gaps 688b may be less than 1.1, less than 1.2, less than 1.5, or less than 2. In an embodiment of the alternative scenario, the third ratio may be 1.

In an embodiment of the alternative scenario, the fourth and fifth radiation beams generated by the radiation sources 720a and 720b respectively may be X-ray beams.

In an embodiment of the alternative scenario, the fourth and fifth radiation beams generated by the radiation sources 720a and 720b respectively may be cone beams.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method, comprising:
    generating 3 radiation beams respectively from 3 locations toward an object and an image sensor, wherein the 3 radiation beams are generated one by one;
    wherein the image sensor comprises (A) an array of M×N active areas, and (B) gaps among the M×N active areas and running in a first direction and a second direction, and
    wherein the first direction is perpendicular to the second direction; and
    capturing 3 partial images of the object with the image sensor, one by one, using respectively radiations of the 3 radiation beams that have passed through and interacted with the object,
    wherein each point of the object is captured in at least one partial image of the 3 partial images, and
    wherein M and N are integers greater than 1.

2. The method of claim 1, further comprising, after said capturing the 3 partial images of the object is performed, stitching the 3 partial images resulting in a stitched image of the object.

3. The method of claim 2, wherein said stitching the 3 partial images comprises projecting at least one partial image of the 3 partial images from one plane to another plane.

4. The method of claim 1, wherein the 3 locations are on a common plane parallel to a surface plane that intersects all sensing elements of the M×N active areas.

5. The method of claim 4, wherein a ratio of a distance between any two locations of the 3 locations to a distance between the common plane and the surface plane is less than 0.1, less than 0.05, less than 0.02, or less than 0.01.

6. The method of claim 1, wherein a straight line connecting any two locations of the 3 locations is not parallel to the first direction and is not parallel to the second direction.

7. The method of claim 6, wherein all the 3 locations are on a straight line.

8. The method of claim 6,
wherein a first ratio of a distance between the first and second locations to a maximum gap width of the gaps is less than 1.5, less than 1.6, less than 1.7, or less than 2, and
wherein a second ratio of a distance between the second and third locations to the maximum gap width of the gaps is less than 1.5, less than 1.6, less than 1.7, or less than 2.

9. The method of claim 8, wherein both the first ratio and the second ratio are in a range of 1.4 to 1.5.

10. The method of claim 1, wherein the 3 radiation beams are X-ray beams.

11. The method of claim 1, wherein the 3 radiation beams are cone beams.

12. A method, comprising:
generating 2 radiation beams respectively from 2 locations toward an object and an image sensor, wherein the 2 radiation beams are generated one by one;
wherein the image sensor comprises (A) an array of 1×N active areas, and (B) gaps among the 1×N active areas and running in a direction; and
capturing 2 partial images of the object with the image sensor, one by one, using respectively radiations of the 2 radiation beams that have passed through and interacted with the object,
wherein each point of the object is captured in at least one partial image of the 2 partial images, and
wherein N is an integer greater than 1.

13. The method of claim 12, further comprising, after said capturing the 2 partial images of the object is performed, stitching the 2 partial images resulting in a stitched image of the object.

14. The method of claim 13, wherein said stitching the 2 partial images comprises projecting at least one partial image of the 2 partial images from one plane to another plane.

15. The method of claim 12, wherein the 2 locations are on a common plane parallel to a surface plane that intersects all sensing elements of the 1×N active areas.

16. The method of claim 15, wherein a ratio of a distance between the 2 locations to a distance between the common plane and the surface plane is less than 0.1, less than 0.05, less than 0.02, or less than 0.01.

17. The method of claim 12, wherein a straight line connecting the 2 locations is not parallel to the direction.

18. The method of claim 17, wherein the straight line connecting the 2 locations is perpendicular to the direction.

19. The method of claim 18, wherein a ratio of a distance between the 2 locations to a maximum gap width of the gaps is less than 1.1, less than 1.2, less than 1.5, or less than 2.

20. The method of claim 19, wherein the ratio is 1.

21. The method of claim 12, wherein the 2 radiation beams are X-ray beams.

22. The method of claim 12, wherein the 2 radiation beams are cone beams.

* * * * *